US007621940B2

(12) United States Patent
Harms et al.

(10) Patent No.: US 7,621,940 B2
(45) Date of Patent: Nov. 24, 2009

(54) ROD-LIKE ELEMENT FOR APPLICATION IN SPINAL OR TRAUMA SURGERY, AND STABILIZATION DEVICE WITH SUCH A ROD-LIKE ELEMENT

(75) Inventors: Jürgen Harms, Karlsruhe (DE); Lutz Biedermann, VS-Villingen (DE); Helmar Rapp, Deisslingen (DE)

(73) Assignee: Biedermann Motech GmbH, VS-Schwenningen (DE)

( * ) Notice: Subject to any disclaimer, the term of this patent is extended or adjusted under 35 U.S.C. 154(b) by 116 days.

(21) Appl. No.: 11/075,235

(22) Filed: Mar. 8, 2005

(65) Prior Publication Data

US 2005/0203519 A1    Sep. 15, 2005

Related U.S. Application Data

(60) Provisional application No. 60/551,937, filed on Mar. 9, 2004.

(30) Foreign Application Priority Data

Mar. 9, 2004   (DE) ................ 10 2004 011 685

(51) Int. Cl.
*A61B 17/70*   (2006.01)
(52) U.S. Cl. .................................... 606/257
(58) Field of Classification Search ............... 606/61, 606/254–258, 260, 265; 623/17.11–17.16; 211/105.5, 105.6; 403/109.3, 118
See application file for complete search history.

(56) References Cited

U.S. PATENT DOCUMENTS

| | | | | |
|---|---|---|---|---|
| 5,062,619 A | * | 11/1991 | Sato | ............... 267/154 |
| 5,180,393 A | * | 1/1993 | Commarmond | ......... 623/13.14 |
| 5,281,222 A | * | 1/1994 | Allard et al. | ................ 606/54 |
| 5,375,823 A | | 12/1994 | Navas | |
| 5,423,816 A | | 6/1995 | Lin | ............... 606/61 |

(Continued)

FOREIGN PATENT DOCUMENTS

DE   693 04 624 T2   4/1997

(Continued)

OTHER PUBLICATIONS

European Search Report dated May 27, 2005 for application No. EP 05 00 2354.

*Primary Examiner*—Thomas C Barrett
*Assistant Examiner*—Nicholas Woodall
(74) *Attorney, Agent, or Firm*—Christie, Parker & Hale LLP

(57) ABSTRACT

A rod-shaped element for use in spinal or trauma surgery, having a first section for connecting to a first bone anchoring element and a second section for connecting to a second bone anchoring element is described. The rod-shaped element also includes a first elastic flexible element that is capable of elastic deformation when a force acts on it transverse to the rod axis. The first section and the second section are capable of shifting relative to each other in the direction of the rod axis.

In a stabilization device for use in spinal or trauma surgery, the rod-shaped element allows for a controlled motion of the parts to be stabilized relative to each other so flexural motion is adjusted separately from the adjustment of the mobility in axial direction.

22 Claims, 3 Drawing Sheets

U.S. PATENT DOCUMENTS

| | | | |
|---|---|---|---|
| 5,480,401 A * | 1/1996 | Navas | 606/256 |
| 5,536,268 A * | 7/1996 | Griss | 606/254 |
| 5,540,688 A * | 7/1996 | Navas | 606/61 |
| 5,961,516 A * | 10/1999 | Graf | 606/256 |
| 6,015,409 A * | 1/2000 | Jackson | 606/278 |
| 6,267,764 B1 | 7/2001 | Elberg | 606/61 |
| 6,328,741 B1 * | 12/2001 | Richelsoph | 606/61 |
| 6,989,011 B2 * | 1/2006 | Paul et al. | 606/61 |
| 2003/0009226 A1 | 1/2003 | Graf | 623/17.6 |
| 2003/0109880 A1 | 6/2003 | Shirado et al. | 606/61 |
| 2003/0220643 A1 * | 11/2003 | Ferree | 606/61 |
| 2004/0049190 A1 | 3/2004 | Biedermann et al. | |
| 2005/0056979 A1 | 3/2005 | Studer et al. | |
| 2005/0085815 A1 | 4/2005 | Harms et al. | |
| 2005/0177157 A1 * | 8/2005 | Jahng | 606/61 |
| 2005/0182400 A1 * | 8/2005 | White | 606/61 |
| 2005/0277922 A1 * | 12/2005 | Trieu et al. | 606/61 |
| 2006/0036240 A1 * | 2/2006 | Colleran et al. | 606/61 |
| 2006/0142758 A1 * | 6/2006 | Petit | 606/61 |
| 2006/0189984 A1 * | 8/2006 | Fallin et al. | 606/61 |
| 2006/0212033 A1 * | 9/2006 | Rothman et al. | 606/61 |
| 2006/0229613 A1 * | 10/2006 | Timm et al. | 606/61 |

FOREIGN PATENT DOCUMENTS

| | | |
|---|---|---|
| DE | 102 36 691 A1 | 2/2004 |
| EP | 0 669 109 B1 | 5/1999 |
| EP | 1 523 949 A1 | 4/2005 |
| GB | 2 382 304 | 5/2003 |
| WO | WO 02102259 A2 * | 12/2002 |
| WO | WO 03/047442 A1 | 6/2003 |

* cited by examiner

ROD-LIKE ELEMENT FOR APPLICATION IN SPINAL OR TRAUMA SURGERY, AND STABILIZATION DEVICE WITH SUCH A ROD-LIKE ELEMENT

REFERENCE TO EARLIER FILED APPLICATIONS

The present invention claims the benefit of the filing date under 35 U.S.C. § 119(e) of Provisional U.S. Patent Application Ser. No. 60/551,937, filed Mar. 9, 2004, which is hereby incorporated by reference. The present application also claims foreign priority benefits pursuant to 35 U.S.C. § 119 (a)-(d) for German Patent Application 10 2004 011 685.7, filed Mar. 9, 2004 in Germany.

BACKGROUND

The present invention relates to a rod-like element for application in spinal or trauma surgery, and a stabilization device using such a rod-like element.

European Patent EP 0 669 109 B1 describes a stabilization device for stabilizing neighboring thoracic vertebrae. The device comprises two pedicle screws and a strap that is fixed in the receiving part of the pedicle screws by a clamping screw. The device contains a support element in the form of a pressure-resistant support body that is mounted on the strap. This stabilization device is not torsion-resistant. Furthermore, the flexural elasticity and the tensile and compression force elasticity are coupled.

U.S. Patent Published Application 2003/0109 880 A1 describes a dynamic stabilization device for vertebrae. The device comprises a first and a second screw to be anchored in the vertebra, each of which has a receiving part for the insertion of a spring connecting the screws, and such a spring. The spring, a helical spring with closely neighboring turns, similar to a helical tension spring, is fixed in the receiving parts by means of clamping screws. This, however, poses the risk that the spring, due to its flexibility, escapes the pressure of the clamping screw, thus causing the connection between the spring and the bone screw to loosen. Moreover, the flexural elasticity and the elasticity with respect to tensile and compression forces are coupled in this device.

German Patent Application DE 102 36 691 A1 describes a dynamic stabilization device for bones, in particular for vertebrae. This device comprises at least two bone anchoring elements and a rigid rod connecting the bone anchoring elements. A spring element is provided on the rod and arranged between the bone anchoring elements. One of the bone anchoring elements is connected to the rod so that it is capable of shifting in the direction of the rod axis, whereby the rod includes a stop for limiting the motion of the anchoring element that is capable of shifting. This stabilization device allows for a translational motion in the direction of the rod axis. In addition, the one anchoring element is capable of shifting relative to the rod and therefore providing for rotational motion of the anchoring element around the rod axis, but not for lateral flexion of the rod.

Therefore, there is a need for dynamic control of motion for the dynamic stabilization of pre-damaged intervertebral disks as well as artificial vertebral disks, in particular those with no inherent mechanism for limiting mobility. Particularly suited for this purpose are stabilization devices with an elastic element, such as the ones described above, which are inserted from the posterior side of the spine.

It is therefore an object of the invention to provide a rod-shaped element for application in spinal or trauma surgery and a stabilization device with such a rod-shaped element which is suited for dynamic posterior stabilization or for dynamic guidance of motion in the presence of a pre-damaged intervertebral disk or in the use of artificial intervertebral disks, in which various degrees of freedom can be adjusted independently of each other.

BRIEF SUMMARY

A rod-shaped element with a rod axis for use in spinal or trauma surgery is described comprising a first section for connecting to a first bone anchoring element; a second section for connecting to a second bone anchoring element and a first flexible element capable of elastic deformation when a forces acts on it transversely to the rod axis, so that the first and second section are capable of shifting or constantly moving relative to each other in the direction of the rod axis.

A stabilization device is described having a first bone anchoring element, a second bone anchoring element and a rod-shaped element. The rod-shaped element comprises a first section for connecting to a first bone anchoring element; a second section for connecting to a second bone anchoring element and a first flexible element capable of elastic deformation when a forces acts on it transversely to the rod axis, so that the first and second section are capable of shifting relative to each other in the direction of the rod axis.

In addition, a method of stabilizing bones or vertebrae is described comprising inserting a first bone anchoring element into a bone or vertebrae, inserting a second bone anchoring element into a second bone or vertebrae and inserting a rod-shaped element into said first and said second bone anchoring elements.

The invention provides the advantage that the elasticity of the connection between two bone anchoring elements with respect to translational motion is decoupled from the flexural elasticity of the rod-shaped element connecting the bone anchoring elements. Connecting the bone anchoring elements by means of the rod-shaped element according to the invention also permits, as an option, free torsional motion around the rod axis, whereby the forces acting on the bone anchoring elements can thus, be reduced.

The foregoing paragraphs have been provided by way of general introduction, and are not intended to limit the scope of the following claims. The presently preferred embodiments, together with further advantages, will be best understood by reference to the following detailed description taken in conjunction with the accompanying drawings.

DETAILED DESCRIPTION OF THE DRAWINGS AND PRESENTLY PREFERRED EMBODIMENTS

The invention and various embodiments thereof are presented in FIGS. 1 to 7 and the accompanying descriptions wherein like numbered items are identical.

Figure 1:
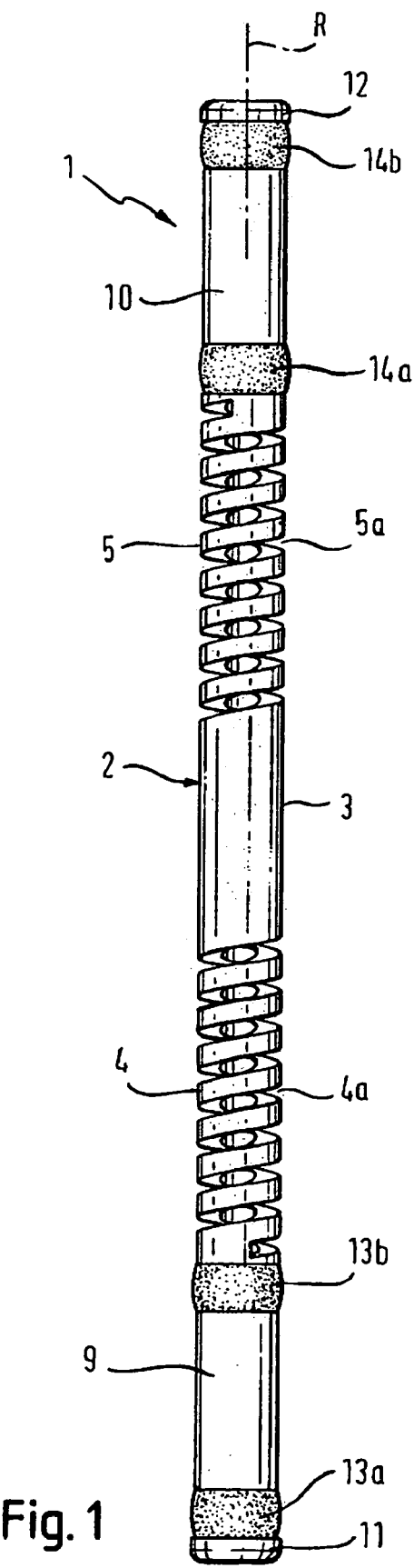
FIG. 1 shows a top view onto the rod-shaped element according to a first embodiment.
Figure 2:
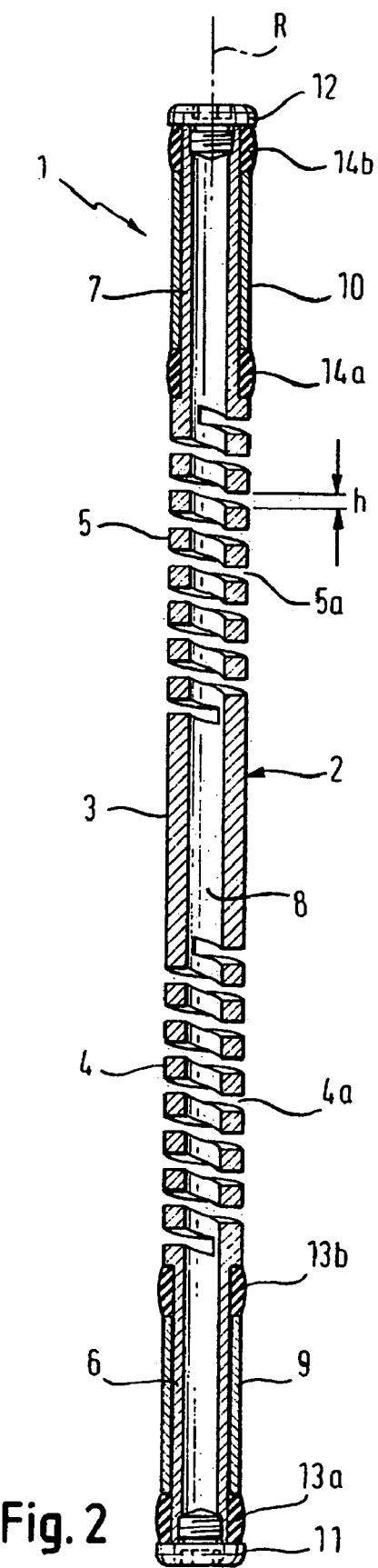
FIG. 2 shows a sectional view of the rod-shaped element of FIG. 1.

As is evident from FIGS. 1 and 2, the rod-shaped element 1 according to a first embodiment comprises a hollow cylindrical rod 2 with a first rigid section 3. The first rigid section 3 has a flexible section 4, 5 on each of its ends. Rigid end sections 6, 7 are attached to flexible sections 4, 5, respectively. In this particular embodiment, flexible sections 4, 5 have the same outer diameter as rigid section 3 which is located between the flexible sections. Rigid end sections 6, 7 have a smaller outer diameter than rigid section 3. In this particular embodiment, the flexible sections 4, 5 are in the form of a spring. Flexible sections 4, 5 are spring sections which are essentially cylindrical having helical turns and recesses 4a or 5a around the cylindrical axis of the rod-shaped element. The spring sections have a pre-determined pitch and length which ends in the radial direction, in the inside portion 8 of rigid section 3. The length of flexible sections 4, 5 in the direction of cylindrical axis R, the height h of helix-shaped recess 4a or 5a, in the direction of the cylinder axis, the pitch of the helix, and the internal diameter of the hollow cylindrical rod are selected so that flexible sections 4, 5 have a desired stiffness with respect to axial forces, flexural forces, i.e. forces acting transverse to the rod axis, and torsional forces.

A sleeve 9, 10 is inserted onto rigid end sections 6, 7, respectively. The inner diameter of the sleeves is slightly larger than the outer diameter of rigid end sections 6, 7 so that sleeve can slide on the rigid end sections. Although described as being inserted by sliding, the sleeves can be inserted onto said rigid section in other ways. The outer diameter of sleeve 9 or 10 corresponds to the outer diameter of the corresponding adjacent flexible section 4 or 5. Preferably, the length of sleeves 9, 10 is smaller than the length of rigid end sections 6, 7.

At the free ends of rigid end sections 6, 7, hollow cylindrical rod 2 includes an internal thread. A securing screw 11, 12 can be inserted into the internal thread. Securing screw 11, 12 each have an outer diameter that is larger than the outer diameter of sleeve 9, 10.

Two elastic rings 13a, 13b or 14a, 14b are provided between sleeve 9 and flexible section 4a and securing screw 11 as well as between sleeve 10 and flexible section 5 and securing screw 12. The elastic rings have an outer diameter which is slightly larger than the outer diameter of sleeve 9, 10. In the unloaded state, elastic rings 13a, 13b, are located at each end of sleeve 9. Elastic rings 14a and 14b are located at each end of sleeve 10 so that the sleeve cannot slip back and forth. The elastic rings are made from a body-compatible elastomer. Body compatible elastomers include but are not limited to polyurethanes or polysiloxanes. Preferably, the elastic rings are made from a body-compatible elastomer having compressible properties. The width of elastic rings 13a, 13b or 14a, 14b in axial direction as well the material of the elastic ring is selected so that sleeve 9, 10 can be shifted a pre-determined degree by compressing the corresponding elastic ring.

The length of rigid section 3 and of rigid end sections 6, 7 as well as the lengths of sleeves 9, 10 in the direction of cylindrical axis R are dimensioned so that each section is at least as large as the diameter of a fixation element (described below) which fixes the rod-shaped element on a bone anchoring element.

Figure 3A:
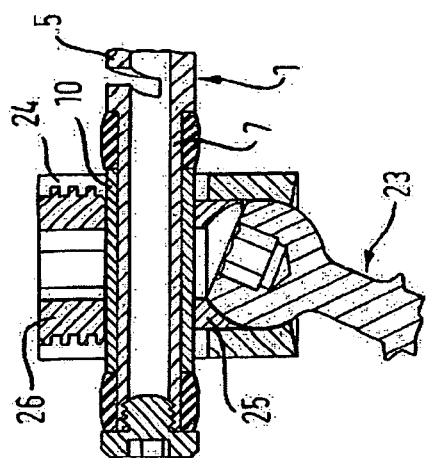
FIG. 3a shows in detail the stabilization device of FIG. 3, in a schematic sectional view.
Figure 3:
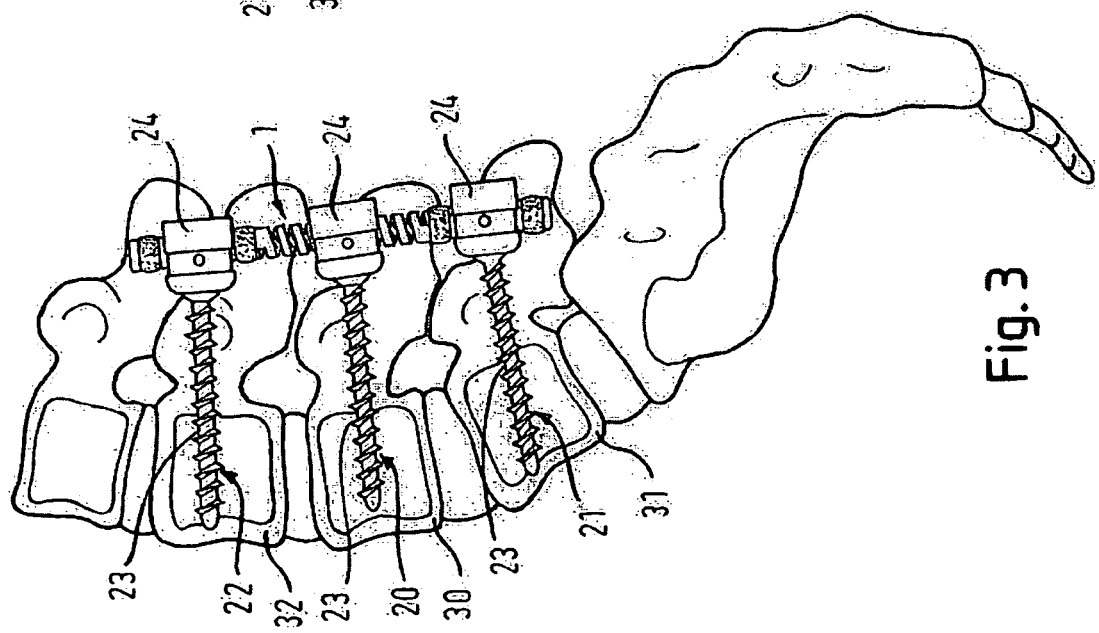
FIG. 3 shows a schematic illustration of an example of application of the rod-element in a first state.

As seen in FIG. 3, the rod-shaped element described above is part of a stabilization device which comprises a first pedicle screw 20, which is connected to rigid section 3 and anchored in a first vertebra 30. The stabilization device also includes a second pedicle screw 21, which is firmly connected to sleeve 9 on rigid end section 6 and anchored in a vertebra 31. The second pedicle screw 21 is adjacent to vertebra 30. A third pedicle screw 22, is firmly connected to sleeve 10 on rigid end section 7 and is anchored in vertebra 32, adjacent to vertebra 30.

As is shown in FIG. 3a, the pedicle screws 20, 21, 22 preferably are polyaxial screws which comprise a screw element 23 and a receiving part 24 flexibly connected thereto, and a pressure piece 25 acting onto the head of screw element 23 and a fixation element 26 for fixing the rod-shaped element in receiving part 24. In the example shown, the receiving part includes a channel for the insertion of the rod-shaped element and an internal screw that can be screwed into the receiving part to hold said rod-shaped element therein. Thus, the length of rigid section 3 and the length of sleeves 9, 10 should be at least equal to the diameter of internal screw 26 which presses onto the rod-shaped element on the various sections.

Although the pedicle screws are described as polyaxial screws, it will be appreciated by those skilled in the art that the pedicle screw can be any type of pedicle screw.

In operation, the pedicle screws are inserted into the vertebrae first, and then the preassembled rod-shaped element, as shown in FIGS. 1 and 2, is placed into and fixed in the receiving parts 24. The pedicle screw 20 of the vertebra 30 in the middle is thereby firmly connected to rigid section 3 of the rod-shaped element, whereas the pedicle screws 21, 22 of the two neighboring vertebrae are firmly connected to sleeves 9, 10, respectively. The rod-shaped element can be manufactured either by the manufacturer or assembled by the surgeon.

Figure 4:
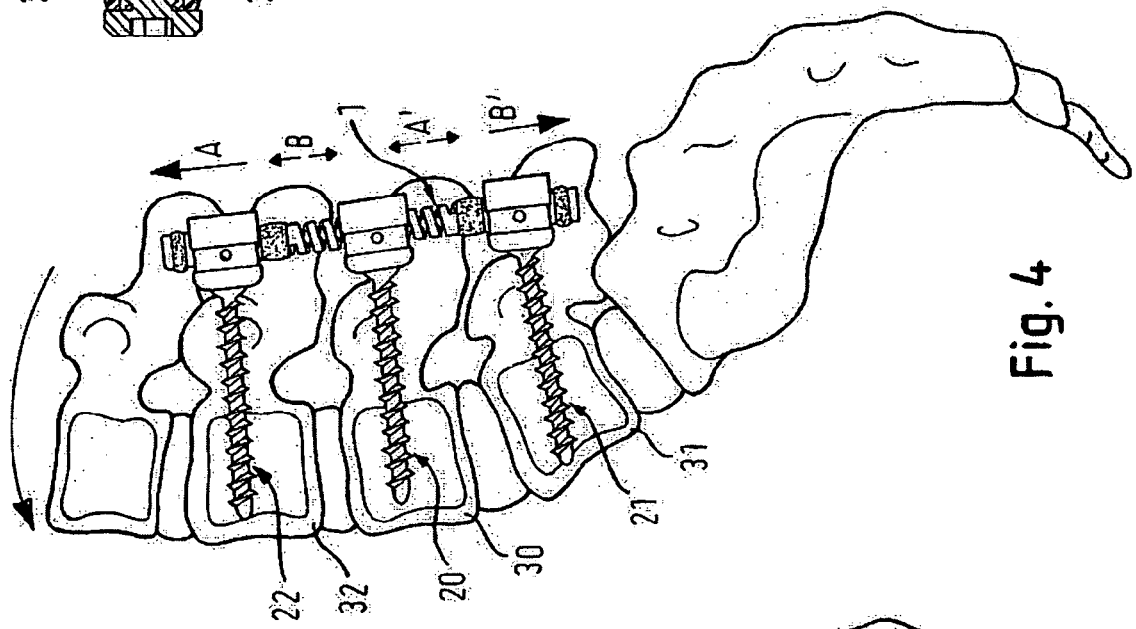
FIG. 4 shows a schematic illustration of the example of FIG. 3 in a second state.

In the multiple-segment stabilization device shown in FIG. 4, the pedicle screw 20 connected to the middle rigid section 3 forms a fixed point for the device during any motion. Upon flexion of the spinal column, flexible sections 4, 5 are extended, causing the distance between pedicle screws 21 and 22 in an axial direction to increase. Simultaneously, sleeves 9, 10 press against and compress their respective outer elastic ring 13a or 14b adjacent to securing screws 11, 12 in this embodiment. The securing screws 11, 12, thereby, form a stop for elastic rings 13a, 14b.

Upon flexion of the spinal column, the outer elastic rings 13a, 14b are initially deformed (illustrated by arrows A, A' in FIG. 4), whereas the flexible sections 4, 5 expand slightly (illustrated by arrows B, B' in FIG. 4). With increasing flexion, the restoring force of the deformed outer elastic rings 13a, 14b increases more as compared to the restoring force of flexible sections 4, 5 ultimately leading to flexible sections 4, 5 having limited mobility, whereas outer elastic rings 13a, 14b have very little additional deformation.

The extension of the spinal column proceeds in an analogous manner against the restoring forces of inner elastic rings 13b, 14a and the restoring force of flexible sections 4, 5.

In the embodiments shown, rotation of the sleeves around cylinder axis R is possible. Torsional forces around the cylinder axis are thereby prevented from acting onto the anchoring of the pedicle screws and loosening them.

In a modification of the first embodiment, the rod-shaped element comprises only one flexible section and one section with a sleeve. The flexible section in this embodiment can be in the form of a spring. This element can be used between two neighboring vertebrae, one anchoring element being firmly connected to the rigid section and the second anchoring element being connected to the corresponding sleeve.

In yet a further modification, the rod-shaped element does not have a rigid section. Rather, the rod-shaped element has two end sections with sleeves and a flexible section extending therebetween.

In a further modification, the diameters of the flexible sections and of the rigid section as well as of the flexible sections between them are varied. In addition, the flexible sections can be made with different elasticities or spring constants. Furthermore, the rod-shaped element is not limited a symmetrical structure as shown in FIGS. 1 to 4, but the rod-shaped element can be nonsymmetrical for example, having sections of varying lengths. Additionally, instead of a securing screw, the rod-shaped element can have a different type of stop, e.g., a fitted ring or similar means.

The anchoring elements can be provided in the form of monoaxial screws or polyaxial screws or as hooks in a known fashion.

Figure 7:
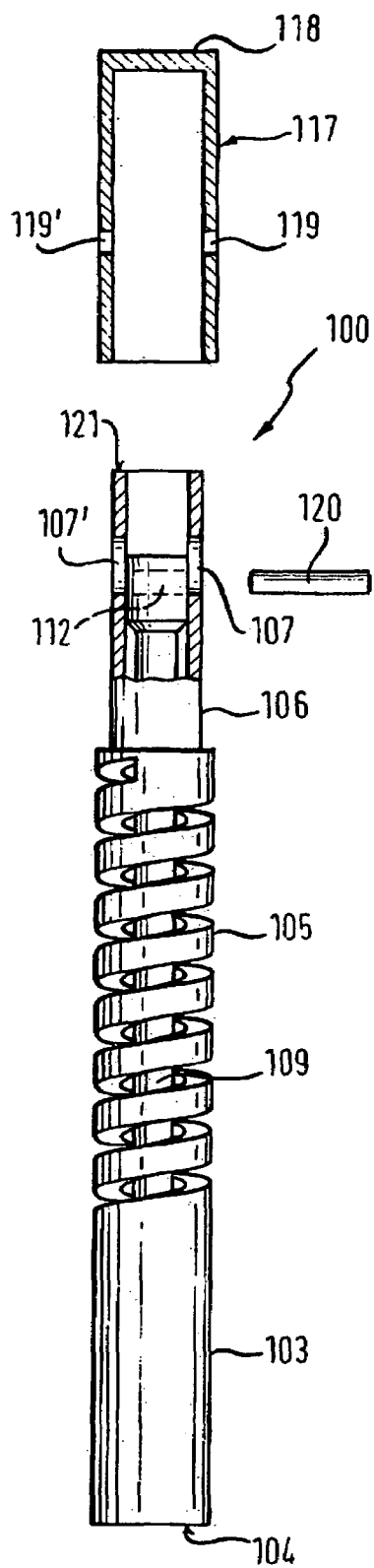
FIG. 7 shows a partial sectional exploded view of the rod-shaped element of FIGS. 5 and 6.
Figure 6:
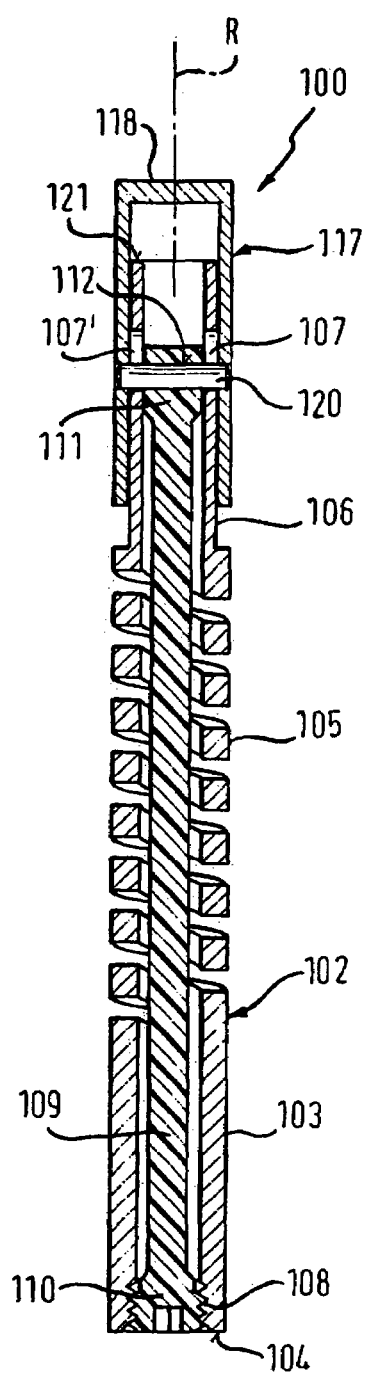
FIG. 6 shows a sectional view of the rod-shaped element according to FIG. 5, rotated by 90°.
Figure 5:
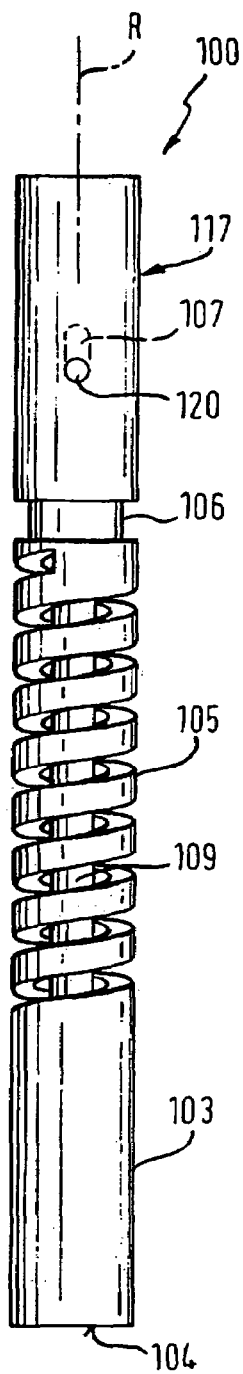
FIG. 5 shows a top view of the rod-shaped element according to a second embodiment.

In a second embodiment shown in FIGS. 5 to 7, the rod-shaped element 100 comprises a hollow cylindrical rod 102 with a first rigid section 103 having a free end 104, a flexible section 105 at one end of the first rigid section 103. A second rigid section 106 having a free end 121 is located adjacent to flexible section 105 and away from the first rigid section 103. The flexible section 105 shown in this embodiment is in the form of a spring. Any other flexible material can be used however to form such flexible section. The flexible section 106, which in this embodiment is shown as a spring is formed by a helix-shaped recess in the wall of hollow cylindrical rod 102, similar to the first embodiment. Flexible section 105 and rigid section 103 have identical outer diameters, whereas the outer diameter of second rigid section 106 is smaller, similar to rigid end section 6 in the first embodiment.

As is seen from FIGS. 6 and 7, rigid end section 106 comprises oblong holes 107, 107' which are located at a pre-determined distance from the free end 121 and off-set from each other by 180°. An internal thread 108 can be found adjacent to a free end of rigid section 103.

Hollow cylindrical rod 102 also includes a flexible element 109, which is essentially rod-shaped and includes at its one end a first connection section 110 with an outer thread which cooperates with internal thread 108 of rigid section 103. Flexible element 109 has a second connection section 111 at its end opposite to the first connection section 110. Second connection section as seen in FIGS. 6 and 7, comprises a bore 112, that is continuous in the radial direction. The length of flexible element 109 is chosen so that when flexible element 109 is attached to the end of rigid section 103 and extended in the direction of the cylindrical axis to a pre-determined length the radial bore 112 coincides with oblong bore holes 107, 107' and/or overlaps with them.

A sleeve 117 having an inner diameter that is larger than the outer diameter of rigid end section 106 is included in the device. Sleeve 117 can be inserted onto the rigid end section 106 by a sliding motion. The outer diameter of sleeve 117 corresponds to the outer diameter of flexible section 105 or of rigid section 103. The sleeve 117 is closed with a cover face 118 on its end, away from the flexible section when in the assembled state.

Sleeve 117 also includes two circular apertures 119, 119' offset from each other by 180° in its outer wall and at a distance from its cover face 118. The diameters of the two circular apertures correspond to the diameter of bore 112 of flexible element 109.

In the assembly of the device, a pin 120 is guided through apertures 119, 119' of sleeve 117 and through oblong holes 107, 107' of rigid end section 106 of the rod, and through bore 112 of flexible element 109. The pin 120 resides in a fitting fashion in apertures 119, 119' and in bore 112. The length of pin 120 is equal to or slightly smaller than the outer diameter of sleeve 117.

The dimensions of rigid section 106 of the rod, the position of oblong holes 107, 107', the length of sleeve 117, and the position of apertures 119, 119' are selected so that, in the assembled state, rigid section 106 is capable of sliding within sleeve 117 over a distance that is defined by the length of the oblong hole which is limited by pin 120 abutting on the oblong hole.

The flexible element is preferably made from an elastic plastic material. End sections 110, 111 for connecting to the end of the rigid section or to the pin are preferably rigid. The remaining part of the rod-shaped element can be made from a body-compatible material, such as titanium, or from a body-compatible plastic material. Preferably a body-compatible metal, such as for instance titanium, or a body-compatible plastic material can be used. Examples of other body-compatible materials include stainless steel, titanium alloys, nickel-titanium alloys, nitinol, chrome alloy, cobalt chrome alloys, shape memory alloys, materials with super elastic properties, carbon reinforced composites, silicone, polyurethane, polyester, polyether, polyalkene, polyethylene, polyamide, poly(vinyl) fluoride, polyetheretherketone (PEEK), polytetrafluoroethylene (PTFE). In addition, the rod-shaped element can be made of shape memory materials or alloys, such as nickel titanium or nitinol.

In operation, rigid section 103 of the rod-shaped element 100 is connected to an anchoring element anchored in the bone, for example with one of the polyaxial screws described above, whereas the other end of the rod-shaped element extending through sleeve 117 is connected to a second bone anchoring element. Although described in this manner, any type of bone anchoring elements can be used. The extension of rod-shaped element 100 from its relaxed state initially causes sleeve 117 to shift relative to rigid section 106, whereas flexible element 105 barely deforms due to its lower elasticity as compared to flexible element 109. Finally, pin 120 reaches the one end of oblong holes 107, 107' thereby preventing any further shifting of sleeve 117 relative to rigid section 106 so that the rod-shaped element can be further extended only against the spring force of flexible section 105. The compression of the rod-shaped element proceeds analogously to the stop of pin 120 on the other end of oblong holes 107, 107' against the restoring force of flexible element 109 by shifting sleeve 117 relative to rigid section 106. Once the pin abuts, the compression of the rod-shaped element proceeds against the restoring force of flexible section 105.

The flexural elasticity of the rod-shaped element, i.e. with respect to the action of forces acting transversely to the rod axis, is determined only by the flexural elasticity of flexible section 105.

In the second embodiment, flexible element 109 assumes the function of elastic rings 13a, 13b, 14a, 14b of the first embodiment, whereas flexible section 105 corresponds to flexible sections 4, 5. However, in contrast to the first embodiment, rotation around cylindrical axis R is not possible with the second embodiment, since rotation is prevented by pin 120 being guided in oblong holes 107, 107'.

In a modification of the second embodiment, the rod-shaped element can be made from multiple segments, as described with the first embodiment. In this embodiment, another flexible section with another sleeve with a symmetrical structure is provided adjacent to free end 104 as shown in FIG. 6. In this embodiment, a second flexible element can be used, or the flexible element shown can be longer and connected in its middle to rigid section 103 by any means, or the flexible element can be longer and guided through the rigid end section but not connected therein.

As before, with the other embodiments, it be appreciated by those of ordinary skill in the art that the individual sections can have different lengths and/or diameters.

Moreover, the rod-shaped elements or sleeves according to the first and second embodiment need not have a circular cross-section, but can have different cross-sections such as for example, an oval or rectangular cross section. By making rigid sections 6, 7 and sleeves 9, 10 with non-circular cross-section, torsional motion can be limited. Flexible sections 4, 5 and 105 need not be springs. If flexible sections 4, 5 and 105 are springs, the sections need not have a helical shape but can be of any other shape.

Flexible element 109 is shown as a rod-like flexible element. Element 109 can, however be of any other shape provided that it is extensible in an elastic fashion. For example, it can be formed as a helical spring or as multiple strands of an elastomeric material.

The elements of the embodiments described above can be combined with each other.

The embodiments described above and shown herein are illustrative and not restrictive. The scope of the invention is indicated by the claims, including all equivalents, rather than by the foregoing description and attached drawings. The invention may be embodied in other specific forms without departing from the spirit and scope of the invention.

We claim:

1. A rod-shaped element having a rod axis, for use in spinal or trauma surgery, comprising:
   a first rigid section configured to connect to a first bone anchoring element;
   a sleeve configured to connect to a second bone anchoring element;
   a second rigid section inside the sleeve, the second rigid section having a first end and a second end;
   a first flexible element capable of elastic deformation when a force acts on said flexible element transversely to the rod axis;
   a second flexible element that dampens movement of the first rigid section relative to the second rigid section in a direction of the rod axis;
   wherein the first rigid section and the second rigid section are capable of constantly moving relative to each other in the direction of the rod axis;
   wherein said first flexible element is connected to the first rigid section on one end of the first flexible element and connected to the second end of the second rigid section on the other end of the first flexible element;
   wherein the sleeve is capable of shifting on said second rigid section a predetermined amount in the direction of the rod axis due to movement of the second flexible element when the sleeve is secured to the second bone anchoring element; and
   wherein most of the sleeve is disposed between the first end of the second rigid section and the second end of the second rigid section.

2. A rod-shaped element according to claim 1, wherein a distance of movement of the sleeve and the second flexible element relative to the second rigid section in the direction of the rod axis are the same when a force acts on the sleeve in the direction of the rod axis.

3. A stabilization device with a first bone anchoring element and a second bone anchoring element and a rod-shaped element according to claim 2.

4. A rod-shaped element according to claim 1, comprising a stop for limiting movement of the sleeve along the second rigid section away from the first flexible element in the direction of the rod axis.

5. A rod-shaped element according to claim 1, wherein said first flexible element is capable of elastic deformation when a force acts on said first flexible element in the direction of the rod axis.

6. A rod-shaped element according to claim 1, wherein the second flexible element includes a damping ring contacting the sleeve adjacent to the sleeve in the direction of the rod axis, the damping ring and the sleeve having substantially similar diameters such that contact is end to end contact.

7. A rod-shaped element according to claim 6, wherein said damping ring is made of an elastic material.

8. A rod-shaped element according to claim 1, wherein the second flexible element comprises a first connection section for connection to the first rigid section and a second connection section for connection to the second rigid section, said second flexible element extending in an axial direction.

9. A rod-shaped element according to claim 8
   wherein the first connection section comprises an outer thread which cooperates with an internal thread of the first rigid section.

10. A rod-shaped element according to claim 9, wherein the second connection section comprises a bore and a pin.

11. A rod-shaped element according to claim 1, wherein the first flexible element and the second flexible element have different elasticities in the direction of the rod axis.

12. A stabilization device with a first bone anchoring element and a second bone anchoring element and a rod-shaped element according to claim 1.

13. The rod-shaped element according to claim 1, wherein when said first flexible element is in use the first rigid section is shifted relative to the second rigid section when a force acts on said first flexible element which elastically deforms said first flexible element.

14. A method of stabilizing two bone or vertebrae with a stabilization device for bone or vertebra comprising a first bone anchoring element having a receiving part, a second bone anchoring element having a receiving part, and a rod-shaped element having a rod axis and comprising a first rigid section, a sleeve, a second rigid section inside the sleeve, and a first flexible element capable of elastic deformation when a force acts on said flexible element transversely to the rod axis, the first flexible element connected to the first rigid section on one end of the first flexible element and connected to the second rigid section on the other end of the first flexible element, the method comprising:
   anchoring the first bone anchoring element in a bone or vertebrae;
   anchoring the second bone anchoring element in a second bone or vertebrae;
   connecting the first rigid section in the receiving part of said first bone anchoring element;
   connecting the sleeve to the receiving part of the second bone anchoring element such that the second bone anchoring element is spaced from the second rigid section by the sleeve being disposed in a space between the receiving part of the second bone anchoring element and the second rigid section;
   wherein the first rigid section and the second rigid section are capable of shifting relative to each other in the direction of the rod axis;
   wherein the sleeve is capable of shifting on said second rigid section a predetermined amount in the direction of the rod axis when the sleeve is fixed to the receiving part of the second bone anchoring element; and wherein most of the sleeve is disposed between a first end of the second rigid section and a second end of the second rigid section.

15. A method of stabilizing bone or vertebrae according to claim 14, wherein said flexible element is capable of elastic deformation when a force acts on said flexible element transversely as well as in the direction of the rod axis.

16. A method of stabilizing bone or vertebrae according to claim 14, further comprising a second flexible element whereby said second flexible element dampens the axial shifting motion of the first rigid section relative to said second rigid section.

17. A method of stabilizing bone or vertebrae with a stabilization device for bone or vertebra comprising a first bone anchoring element having a receiving part, a second bone anchoring element having a receiving part, and a rod-shaped element having a rod axis and comprising a first rigid section, a sleeve, a second rigid section inside the sleeve, and a first flexible element capable of elastic deformation when a force acts on said flexible element transversely to the rod axis, the first flexible element connected to the first rigid section on one end of the first flexible element and connected to the second rigid section on the other end of the first flexible element, wherein the first rigid section is connected to the receiving part of the first bone anchoring element, wherein the sleeve is connected to and contacts the receiving part of the second bone anchoring element such that the second bone anchoring element is spaced from the second rigid section by the sleeve being disposed in a space between the receiving part of the second bone anchoring element and the second rigid section, and wherein the second rigid section is shiftably coupled to the second bone anchoring element in a direction of the rod axis when the sleeve is fixed to the receiving part of the second bone anchoring element, the method comprising:

anchoring the first bone anchoring element to a first bone or vertebrae;

anchoring the second bone anchoring element to a second bone or vertebrae;

mounting the sleeve inside the receiving part of the second bone anchoring element;

fixing the sleeve to the receiving part of the second bone anchoring element; and connecting the first rigid section of the rod-shaped element to said first bone anchoring element, wherein a translational elasticity between the bone anchoring elements is decoupled from the flexural elasticity of the rod-shaped implant by the sleeve being shiftable relative to the second rigid section.

18. A stabilization device for bone or vertebra comprising:
a first bone anchoring element having a receiving part;
a second bone anchoring element having a receiving part; and
a rod-shaped element having a rod axis and comprising:
a first rigid section;
a sleeve;
a second rigid section inside the sleeve; and
a first flexible element capable of elastic deformation when a force acts on said flexible element transversely to the rod axis, the first flexible element connected to the first rigid section on one end of the first flexible element and connected to the second rigid section on the other end of the first flexible element;
wherein the first rigid section is connected to the receiving part of the first bone anchoring element;
wherein the sleeve is connected to and contacts the receiving part of the second bone anchoring element such that the second bone anchoring element is spaced from the second rigid section by the sleeve being disposed in a space between the receiving part of the second bone anchoring element and the second rigid section; and
wherein the sleeve is capable of shifting on said second rigid section a predetermined amount in a direction of the rod axis when the sleeve is fixed to the receiving part of the second bone anchoring element.

19. A rod-shaped element according to claim 18, wherein the first rigid section and the second rigid section are shiftable relative to each other about the rod axis when the sleeve is fixed to the receiving part of the second bone anchoring element.

20. A rod-shaped element according to claim 18, wherein the first rigid section and the second rigid section are secured against shifting about the rod axis when the sleeve is fixed to the receiving part of the second bone anchoring element.

21. A stabilization device according to claim 18
wherein the second rigid section has a first end and a second end and most of the sleeve is mounted on the second rigid section.

22. A stabilization device according to claim 18 further comprising
a second flexible element that dampens movement of the first rigid section relative to the second rigid section in a direction of the rod axis,
wherein the sleeve shifts on said second rigid section the predetermined amount in the direction of the rod axis due to movement of the second flexible element when the sleeve is fixed to the second bone anchoring element.

\* \* \* \* \*

UNITED STATES PATENT AND TRADEMARK OFFICE
CERTIFICATE OF CORRECTION

| | | |
|---|---|---|
| PATENT NO. | : 7,621,940 B2 | Page 1 of 1 |
| APPLICATION NO. | : 11/075235 | |
| DATED | : November 24, 2009 | |
| INVENTOR(S) | : Jürgen Harms et al. | |

It is certified that error appears in the above-identified patent and that said Letters Patent is hereby corrected as shown below:

Title page, item (*) Notice: Subject to any disclaimer, the term of this patent is extended or adjusted under 35 U.S.C. 154(b) by 116 days.

Delete the phrase "by 116 days" and insert -- by 279 days --.

Column 2, line 56                     Delete "rod-element"
                                      Insert -- rod-shaped element --.

Column 2, line 14                     Delete "forces"
                                      Insert -- force --.

Column 2, line 24                     Delete "forces"
                                      Insert -- force --.

Column 7, line 3                      After "it"
                                      Insert -- can --.

Column 5, line 10                     Before "a"
                                      Insert -- to --.

Signed and Sealed this

Fourteenth Day of September, 2010

David J. Kappos
*Director of the United States Patent and Trademark Office*